(12) United States Patent
Holmberg

(10) Patent No.: US 8,417,349 B2
(45) Date of Patent: Apr. 9, 2013

(54) RATE MATCHING FOR A STIMULATING MEDICAL DEVICE

(75) Inventor: Paul Holmberg, Sydney (AU)

(73) Assignee: Cochlear Limited, Macquarie University, NSW (AU)

( * ) Notice: Subject to any disclaimer, the term of this patent is extended or adjusted under 35 U.S.C. 154(b) by 112 days.

(21) Appl. No.: 12/835,649

(22) Filed: Jul. 13, 2010

(65) Prior Publication Data
US 2012/0016443 A1 Jan. 19, 2012

(51) Int. Cl.
*A61N 1/00* (2006.01)
(52) U.S. Cl.
USPC .......................................................... 607/57
(58) Field of Classification Search ............... 607/57, 607/509
See application file for complete search history.

(56) References Cited

U.S. PATENT DOCUMENTS

2012/0004705 A1* 1/2012 James .......................... 607/57

* cited by examiner

*Primary Examiner* — George Manuel
*Assistant Examiner* — Robert N Wieland
(74) *Attorney, Agent, or Firm* — Kilpatrick, Townsend & Stockton, LLP.

(57) ABSTRACT

Methods and systems are disclosed for rate matching in a stimulating medical device, such as a cochlear implant or an auditory brain stimulator. In embodiments, the stimulating medical device applies a fast Fourier transform (FFT) at an analysis rate to the received signal to obtain a plurality frequency bin output signals. The stimulating medical device then applies a rate matching through interpolation function to the frequency bin output signals to match the stimulation rate for the stimulating medical device. This rate matching through interpolation function may apply a common interpolation filter to each frequency bin output to obtain a plurality of outputs distributed in time across the time period between executions of the FFT. The values of the frequency bin output signals at the time most closely matching the time for which stimulation is to be applied may then be selected and used in applying the stimulation.

34 Claims, 13 Drawing Sheets

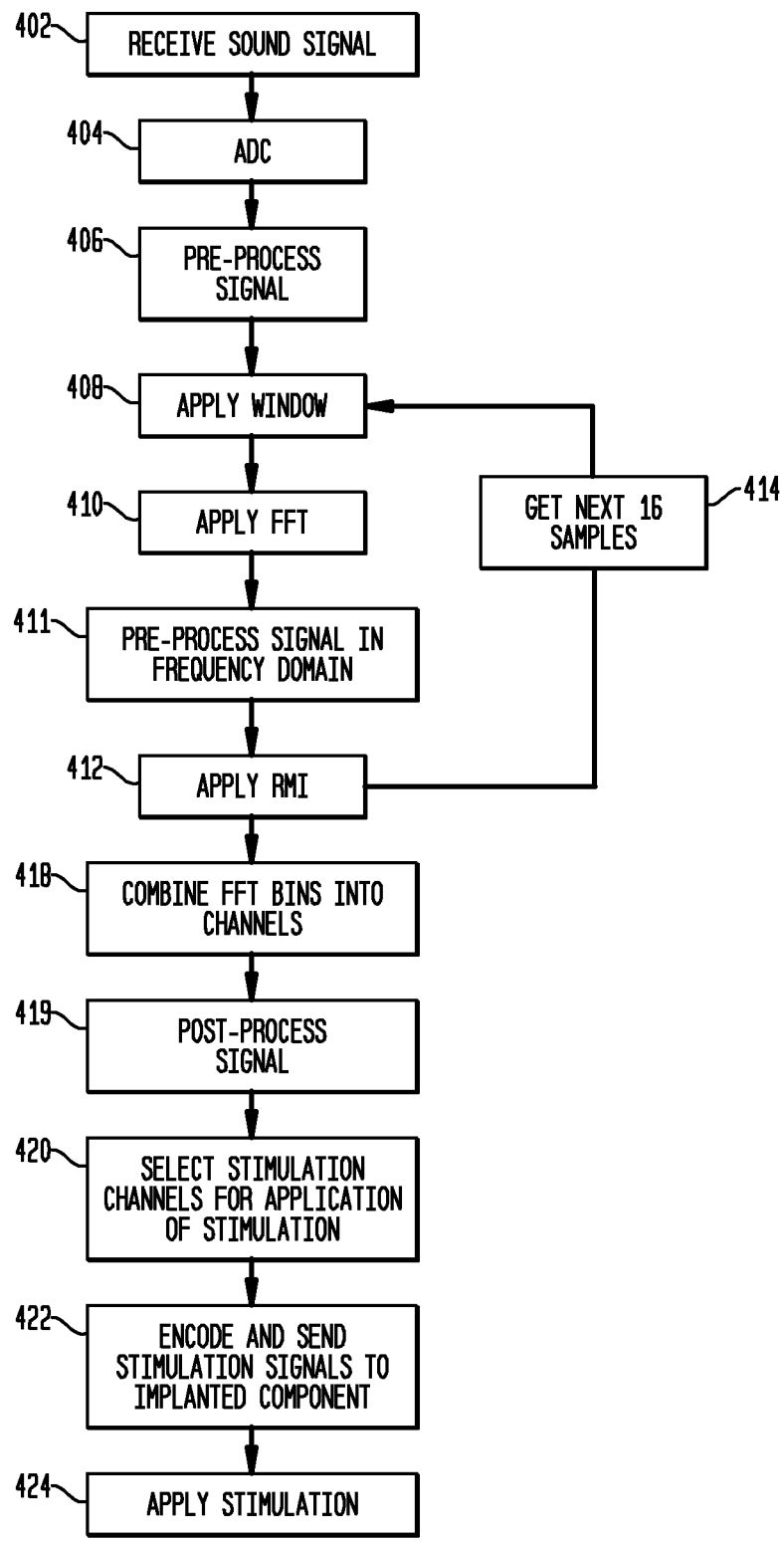

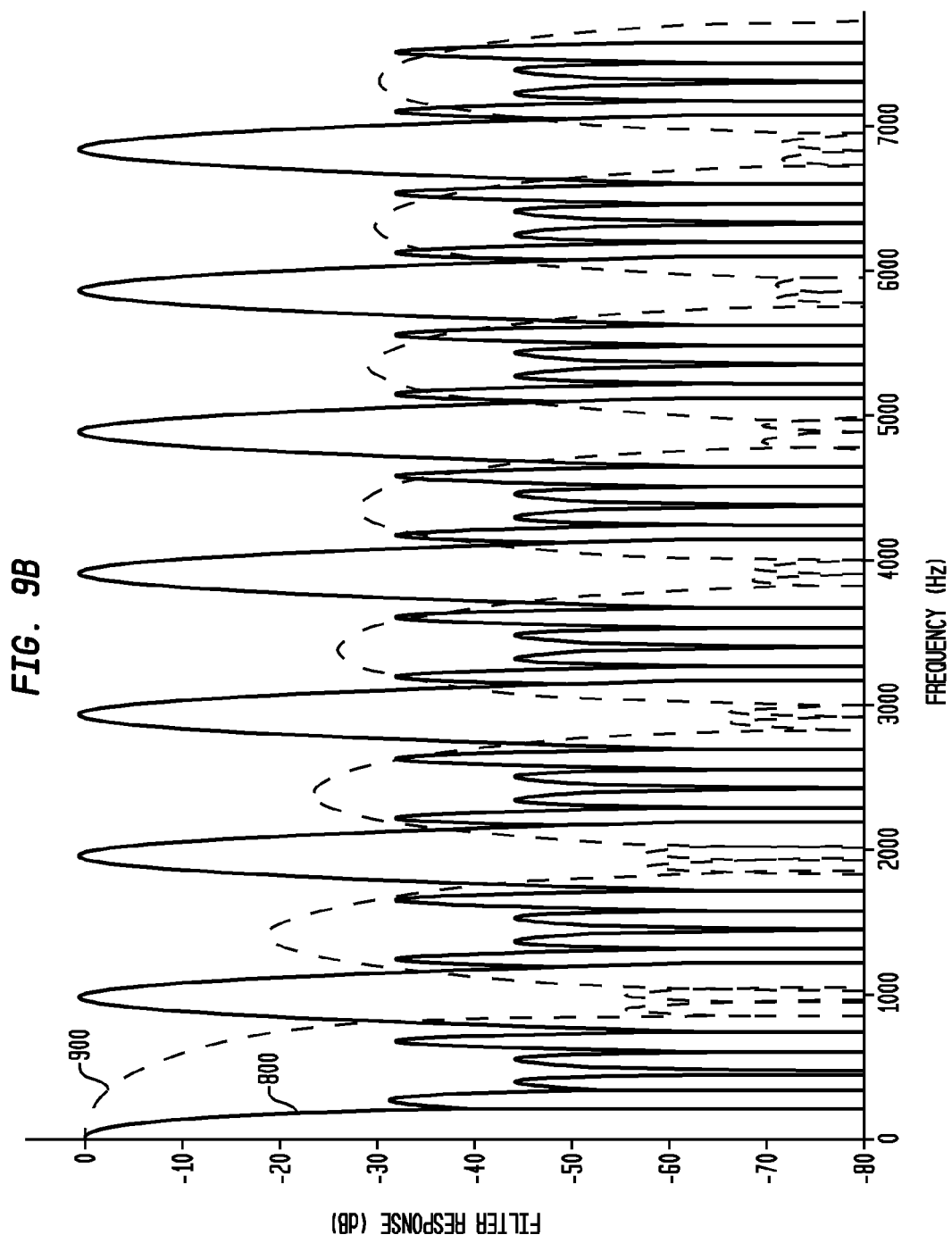

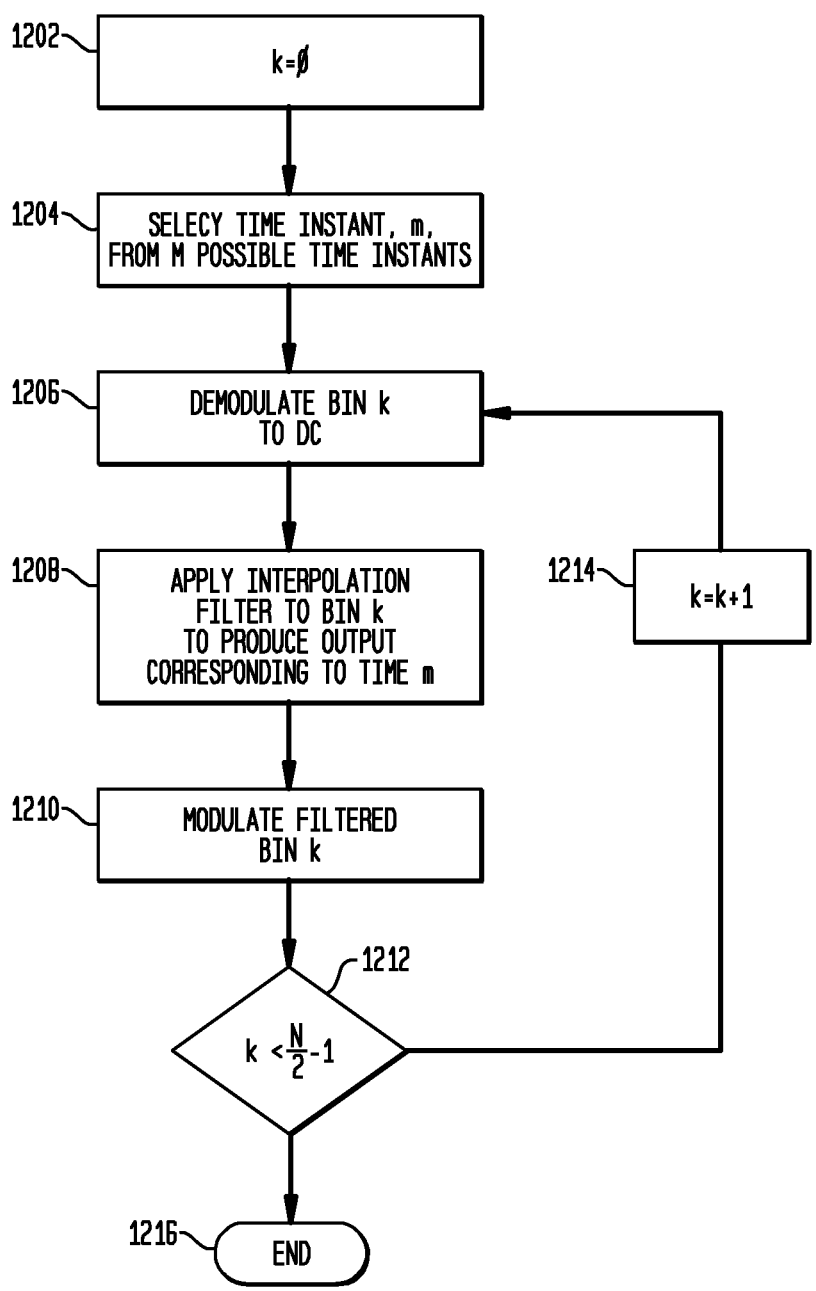

RATE MATCHING FOR A STIMULATING MEDICAL DEVICE

BACKGROUND

1. Field of the Invention

The present invention relates generally to a stimulating medical device, and more particularly, to rate matching in applying stimulation by the stimulating medical device.

2. Related Art

Hearing loss, which may be due to many different causes, is generally of two types, conductive and sensorineural. In some cases, a person may have hearing loss of both types. Conductive hearing loss occurs when the normal mechanical pathways for sound to reach the hair cells in the cochlea are impeded, for example, by damage to the ossicles. Conductive hearing loss is often addressed with conventional hearing aids which amplify sound so that acoustic information can reach the cochlea.

In many people who are profoundly deaf, however, the reason for their deafness is sensorineural hearing loss. Sensorineural hearing loss occurs when there is damage to the inner ear or to the nerve pathways from the inner ear to the brain. Those suffering from sensorineural hearing loss are thus unable to derive suitable benefit from conventional hearing aids. As a result, hearing prostheses that deliver electrical stimulation to nerve cells of the recipient's auditory system have been developed to provide persons having sensorineural hearing loss with the ability to perceive sound. Such stimulating hearing prostheses include, for example, auditory brain stimulators and cochlear prostheses (commonly referred to as cochlear prosthetic devices, cochlear implants, cochlear devices, and the like; simply "cochlea implants" herein.) As used herein, the recipient's auditory system includes all sensory system components used to perceive a sound signal, such as hearing sensation receptors, neural pathways, including the auditory nerve and spiral ganglion, and parts of the brain used to sense sounds.

Most sensorineural hearing loss is due to the absence or destruction of the cochlear hair cells which transduce acoustic signals into nerve impulses. It is for this purpose that cochlear implants have been developed. Cochlear implants use direct electrical stimulation of auditory nerve cells to bypass absent or defective hair cells that normally transduce acoustic vibrations into neural activity. Such devices generally use an electrode array implanted into the scala tympani of the cochlea so that the electrodes may differentially activate auditory neurons that normally encode differential frequencies of sound.

Auditory brain stimulators are used to treat a smaller number of recipients with bilateral degeneration of the auditory nerve. For such recipients, the auditory brain stimulator provides stimulation of the cochlear nucleus in the brainstem.

In applying electrical stimulation to a recipient, medical devices, such as cochlear implants and auditory brain stimulators, apply stimulation to the recipient at a stimulation rate. The stimulation rate is typically dependent on the preferences and psychophysical effects of individual recipients, as well as system limitations of the medical device itself. Traditional audio processing algorithms typically use fixed rate analysis rates for improved efficiency and simplification of implementation. The stimulation rate thus is often different than the analysis rate for the device.

SUMMARY

In one aspect of the present invention there is provided a method for delivering a stimulating signal by a stimulating medical device having a plurality of electrodes, comprising: receiving a sound signal; applying a fast Fourier transform (FFT) to the received signal to obtain a first set of one or more frequency bin outputs at an analysis time; applying an interpolation filter to a first one of the one or more frequency bin outputs to interpolate a value of the first frequency bin for a stimulation time; applying the interpolation filter to a second one of the one or more frequency bin outputs to interpolate a value of the second frequency bin for the stimulation time; and delivering a stimulation signal at the stimulation time by the stimulation medical device via at least one of the electrodes using the interpolated value of the first frequency bin and/or the interpolated value of the second frequency bin.

In another aspect there is provided a stimulating medical device for delivering stimulation to a recipient, comprising: at least one electrode configured to deliver stimulation to the recipient; a sound input device configured to receive a sound signal; a sound processor comprising: an fast Fourier transform (FFT) functional block configured to apply an FFT to the received signal to obtain a first set of one or more frequency bin outputs at an analysis time; an interpolation functional block configured to apply an interpolation filter to a first one of the one or more frequency bin outputs to interpolate a value of the first frequency bin for a stimulation time; and apply the interpolation filter to a second one of the one or more frequency bin outputs to interpolate a value of the second frequency bin for the stimulation time; and a stimulator unit configured to deliver a stimulation signal at the stimulation time by the stimulation medical device via at least one of the electrodes using the interpolated value of the first frequency bin and/or the interpolated value of the second frequency bin.

In yet another aspect there is provided a system for delivering a stimulating signal to a recipient, comprising: means for receiving a sound signal; means for applying a fast Fourier transform (FFT) to the received signal to obtain a first set of one or more frequency bin outputs at an analysis time; means for applying an interpolation filter to a first one of the one or more frequency bin outputs to interpolate a value of the first frequency bin for a stimulation time; means for applying the interpolation filter to a second one of the one or more frequency bin outputs to interpolate a value of the second frequency bin for the stimulation time; and means for delivering a stimulation signal at the stimulation time by the stimulation medical device via at least one of the electrodes using the interpolated value of the first frequency bin and/or the interpolated value of the second frequency bin.

BRIEF DESCRIPTION OF THE DRAWINGS

Embodiments of the present invention are described below with reference to the attached drawings, in which:

FIG. 4 provides a flow chart for receiving sound signals and applying stimulation, in accordance with an embodiment of the present invention;

FIG. 9B illustrates the frequency response of FIG. 8 overlaid with the frequency response of FIG. 9A;

FIG. 12 provides an exemplary flow chart for application of rate matching by interpolation function, in accordance with an embodiment of the present invention.

DETAILED DESCRIPTION

Figure 1:
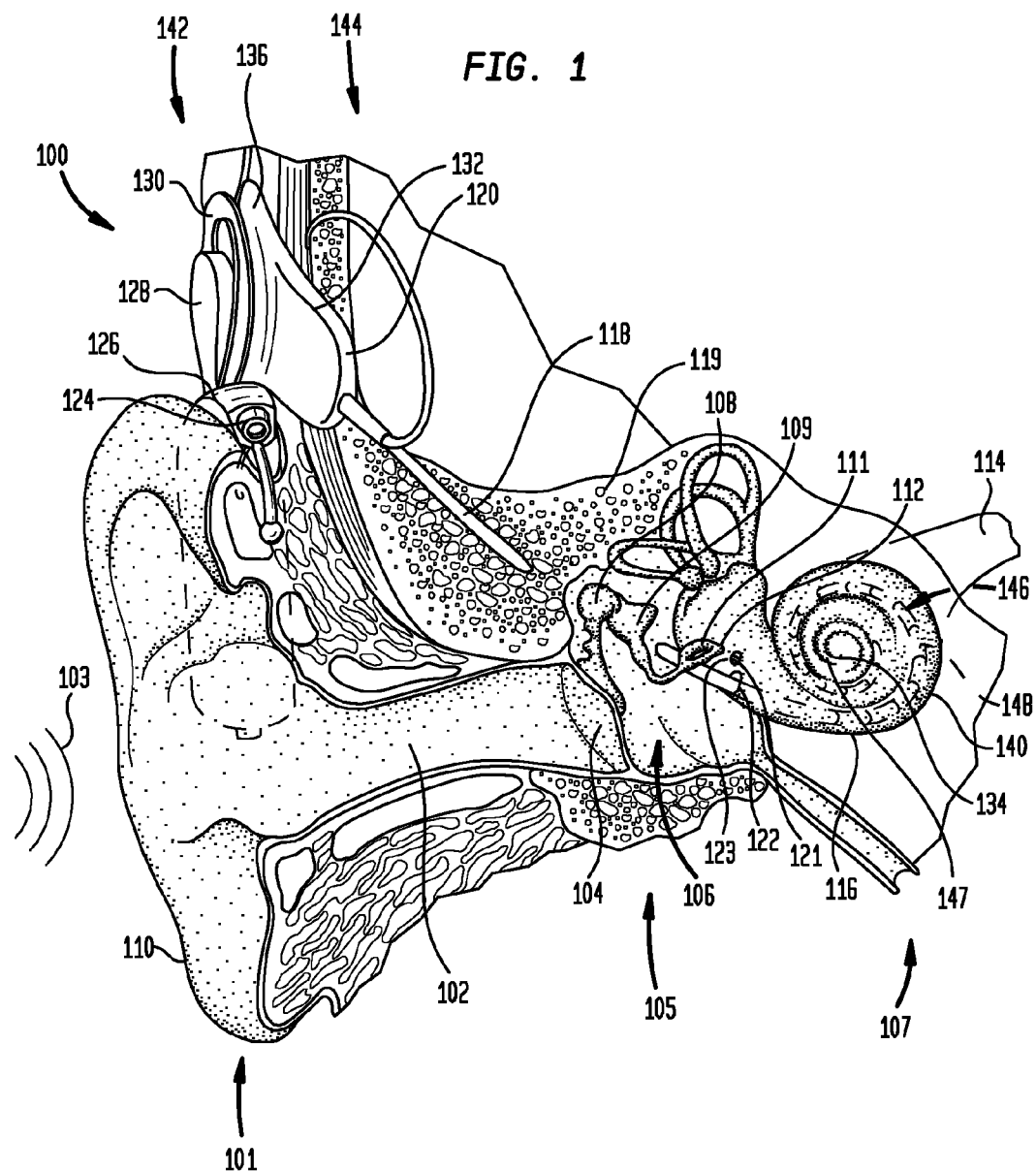
FIG. 1 is a perspective view of a cochlear implant in which embodiments of the present invention may be implemented.

Aspects of the present invention are generally directed rate matching in applying stimulation by a stimulating medical device, such as a cochlear implant or an auditory brain stimulator. In embodiments, the stimulating medical device applies a Fast Fourier Transform (FFT) to a received sound signal to obtain a plurality of frequency bin outputs. This FFT may operate at fixed analysis rate; and, for example, may operate at a specified overlap rate. In an embodiment, the FFT may be a 128 point FFT that is executed every 16 new received samples. Thus, in this exemplary embodiment, ⅞ths of the 128 samples for the FFT are old samples and 16 are new samples, for an overlap rate of N*⅞, where N=128. It should be noted, however, that in other embodiments, different FFT sizes may be used (e.g., 64, 256, 512, etc.) as well as different overlap rates.

An interpolation filter is then applied to a plurality of the frequency bin outputs to obtain an interpolated value for each of the frequency bins at the stimulation time (i.e., the time at which stimulation is applied), which may be different than the analysis time (i.e., the time at which the FFT is executed). For example, in an embodiment, the analysis rate (e.g., the rate at which the FFT is executed) may be different than the stimulation rate (e.g., the rate at which stimulation is applied).

This interpolation filter may be determined for the DC frequency bin of the FFT, such as, for example, to reduce the amplitudes of images appearing in a frequency response associated with the DC bin. Then, this interpolation filter may be applied to each frequency bin by, for example, modulating the determined interpolation filter to the frequency corresponding to the bin and applying the modulated interpolation filter to the frequency bin output. Or, for example, the frequency bin output may be demodulated to DC, the interpolation filter applied, and the resulting signal modulated back to the frequency corresponding to the FFT frequency bin.

In an embodiment. application of this interpolation filter to each of the FFT frequency bins may result in a plurality of interpolated values for the frequency bin distributed in time across the period of time (e.g., the analysis period or another specified period of time). The stimulating medical device may then select the values for these bins at the time most closely matching the time at which the stimulating medical device intends to apply stimulation. In this manner, the stimulating medical device may match the rate at which the FFT is executed (referred to as the analysis rate) to the rate at which stimulation is applied by the stimulating medical device (referred to as the stimulation rate). In another embodiment, rather than outputting a plurality of interpolated values distributed across the analysis period (or other period of time), the particular output time of the interpolation filter corresponding to the desired stimulation time may be determined; and, then the interpolation filter may be used to only calculate the interpolated value of the frequency bins for this determined output time.

Embodiments of the present invention are described herein primarily in connection with one type of hearing prosthesis, namely a cochlear prostheses (commonly referred to as cochlear prosthetic devices, cochlear implants, cochlear devices, and the like; simply "cochlea implants" herein.) Cochlear implants generally refer to hearing prostheses that deliver electrical stimulation to the cochlea of a recipient. As used herein, cochlear implants also include hearing prostheses that deliver electrical stimulation in combination with other types of stimulation, such as acoustic or mechanical stimulation. It would be appreciated that embodiments of the present invention may be implemented in any cochlear implant or other hearing prosthesis now known or later developed, including auditory brain stimulators, or implantable hearing prostheses that acoustically and/or mechanically stimulate components of the recipient's middle or inner ear.

Figure 2:
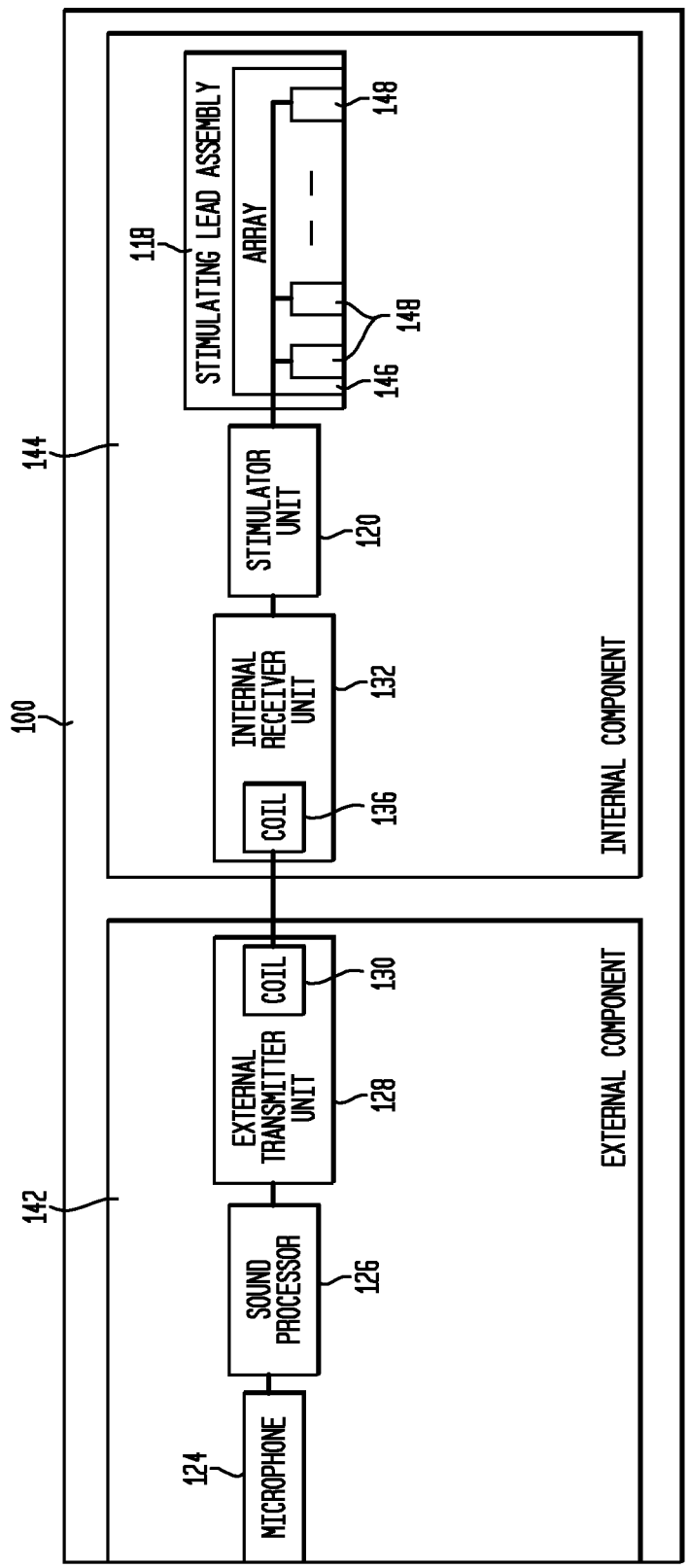
FIG. 2 is a functional block diagram of the cochlear implant of FIG. 1, in accordance with an embodiment of the present invention.

FIG. 1 is perspective view of a cochlear implant, referred to as cochlear implant 100 implanted in a recipient. FIG. 2 is a functional block diagram of cochlear implant 100. The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant 100 comprises an external component 142 which is directly or indirectly attached to the body of the recipient, and an internal component 144 which is temporarily or permanently implanted in the recipient. External component 142 typically comprises one or more sound input elements, such as microphone 124 for detecting sound, a sound processor 126, a power source (not shown), and an external transmitter unit 128. External transmitter unit 128 comprises an external coil 130 and, preferably, a magnet (not shown) secured directly or indirectly to external coil 130. Sound processor 126 processes the output of microphone 124 that is positioned, in the depicted embodiment, by auricle 110 of the recipient. Sound processor 126 generates encoded signals, sometimes referred to herein as encoded data signals, which are provided to external transmitter unit 128 via a cable (not shown). Sound processor 126 may further comprise a data input interface (not shown) that may be used to connect sound processor 126 to a data source, such as a personal computer or musical instrument (e.g., a MIDI instrument).

Internal component 144 comprises an internal receiver unit 132, a stimulator unit 120, and a stimulating lead assembly 118. Internal receiver unit 132 comprises an internal coil 136, and preferably, a magnet (also not shown) fixed relative to the internal coil. Internal receiver unit 132 and stimulator unit 120 are hermetically sealed within a biocompatible housing, sometimes collectively referred to as a stimulator/receiver unit. The internal coil receives power and stimulation data from external coil 130. Stimulating lead assembly 118 has a proximal end connected to stimulator unit 120, and a distal end implanted in cochlea 140. Stimulating lead assembly 118 extends from stimulator unit 120 to cochlea 140 through mastoid bone 119. In some embodiments stimulating lead assembly 118 may be implanted at least in basal region 116, and sometimes further. For example, stimulating lead assembly 118 may extend towards apical end of cochlea 140, referred to as cochlea apex 134. In certain circumstances, stimulating lead assembly 118 may be inserted into cochlea 140 via a cochleostomy 122. In other circumstances, a cochleostomy may be formed through round window 121, oval window 112, the promontory 123 or through an apical turn 147 of cochlea 140.

Stimulating lead assembly 118 comprises a longitudinally aligned and distally extending array 146 of electrode contacts 148, sometimes referred to as array of electrode contacts 146 herein. Although array of electrode contacts 146 may be disposed on stimulating lead assembly 118, in most practical applications, array of electrode contacts 146 is integrated into stimulating lead assembly 118. As such, array of electrode contacts 146 is referred to herein as being disposed in stimulating lead assembly 118. Stimulator unit 120 generates stimulation signals which are applied by electrode contacts 148 to cochlea 140, thereby stimulating auditory nerve 114. Because, in cochlear implant 100, stimulating lead assembly 118 provides stimulation, stimulating lead assembly 118 is sometimes referred to as a stimulating lead assembly.

In cochlear implant 100, external coil 130 transmits electrical signals (that is, power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding (not shown). In use, implantable receiver unit 132 may be positioned in a recess of the temporal bone adjacent auricle 110 of the recipient. Cochlear implant 100 may, for example, resemble a cochlear implant current used for implementing the Advanced Combination Encoder (ACE) sound coding scheme.

Figure 3:
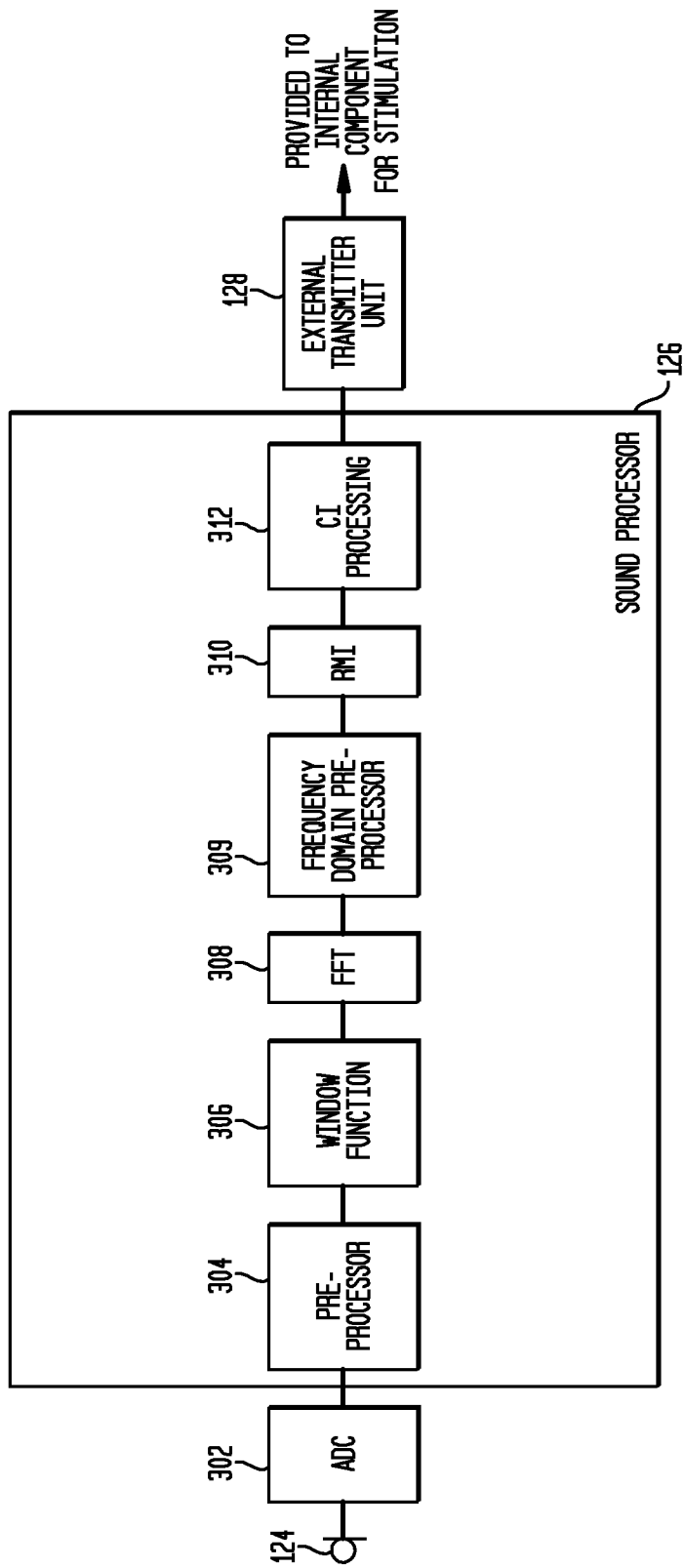
FIG. 3 illustrates a functional diagram of an exemplary sound processor, in accordance with an embodiment of the present invention.

FIG. 3 illustrates a functional diagram of an exemplary sound processor 126, in accordance with an embodiment. FIG. 4 provides a flow chart for receiving sound signals and applying stimulation, in accordance with an embodiment. FIG. 4 will be discussed with reference to FIG. 3.

As illustrated, sound processor 126 receives input from one or more sound input devices, such as microphone 124 at block 402. It should be appreciated, however, that any sound input device now or later developed may be used to provide one or more input sound signals. For example, in an embodiment, the sound input device may be, for example, an input jack for receiving a signal from, for example, the headphone jack of an MP3 player or other audio device.

As illustrated, the output of microphone 124 is provided to an Analog to Digital Converter (ADC) 302 that converts the analog microphone signal to a digital signal at block 404. The output of ADC 302 is provided to a pre-processor 304 that pre-processes the signal at block 406. Pre-processor 304 may, for example, use a pre-emphasis filter, automatic gain control (AGC), and/or manual sensitivity control (MSC), and other signal pre-processing components. The structure and operation of preprocessor 304 is considered to be well-known in the art and, therefore, is not described further herein.

Pre-processor 304 provides its output to an optional windowing function 306, which applies a window to digitized signal from pre-processor 304 at block 408. The windowing function 306 provides its output to a Fast Fourier Transform (FFT) 308 at block 410. In an embodiment, the FFT may be a 128-point FFT; however, in other embodiments different sizes, such as, for example, a 64 point FFT or 256 point FFT. In an embodiment, the windowing function may be applied to the inputs to FFT 308 to improve performance of the FFT and prevent spectral leakage.

In an embodiment in which the FFT is a 128 point FFT, the windowing function 306 may be symmetric 128 point Hann window (also referred to as a Hanning window) with no leading or trailing zeros. For example, in an embodiment, the Hann window may be in accordance with the following formula:

$$w(n) = 0.5\left(1 - \cos\left(\frac{2\pi(n)}{N+1}\right)\right)$$

Where: N=Number of Data Points (128), and n=[1 . . . N]

Figure 5A:
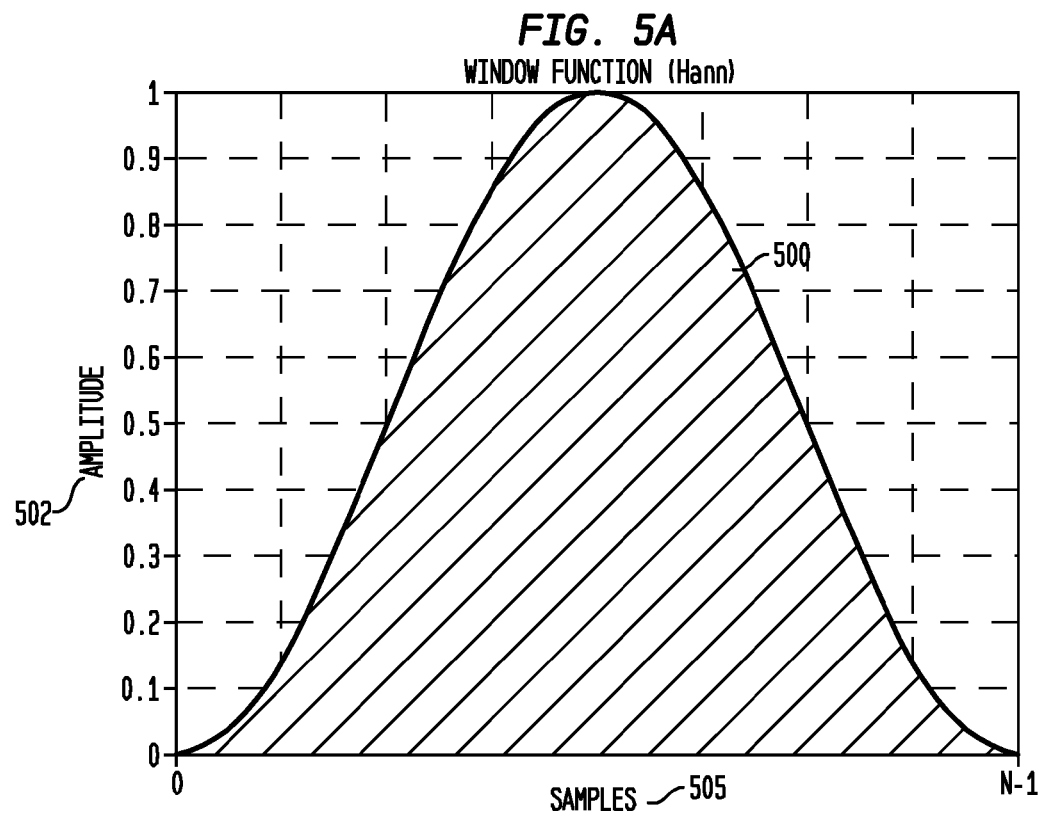
FIG. 5A illustrates a window that may be applied to a received signal, in accordance with an embodiment of the invention.
Figure 5B:
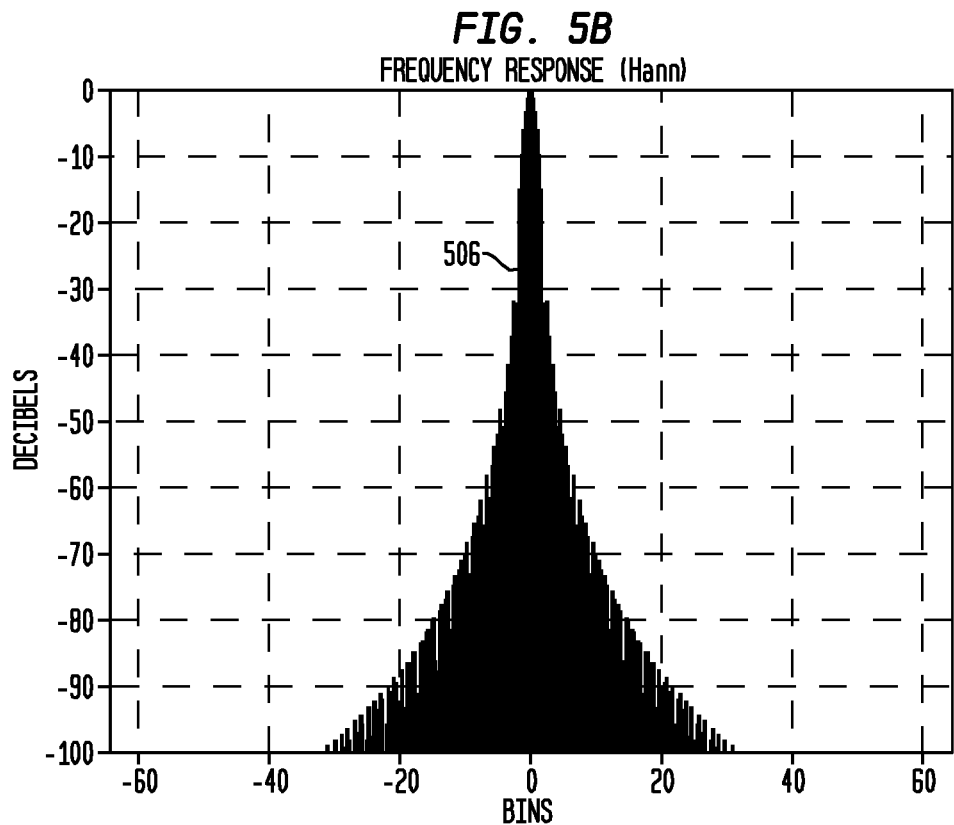
FIG. 5B illustrates the frequency response of the exemplary window of FIG. 5A.

FIGS. 5A and 5B illustrate an exemplary windowing function, in accordance with an embodiment of the invention. FIG. 5A illustrates the amplitude 502 of the window 500 versus sample number 505. FIG. 5B illustrates the frequency response 506 of the exemplary window. Particularly, FIG. 5B illustrates the amplitude in terms of decibels (dB) of the exemplary window versus frequency bin (ranging from −(N/2) to +(N/2)). In this example, the windowing function is a Hann window. As shown, in FIG. 5A, the window 500 may comprise a bell shape with a peak centered at N/2 (e.g., 64). Similarly, the frequency response of the window may have a peak at bin 0. As illustrated, the exemplary window of FIGS. 5A-5B is symmetrical. In an embodiment, this symmetry may be harnessed by signal processing unit 126 storing only 64 if the 128 samples.

As noted above, the FFT 308 may be a 128 point FFT. For example, the FFT 308 may be a 128 point FFT radix-2 decimation in time FFT that operates on time domain audio samples received from the windowing function 306. In such an example, the FFT 308 receives 128 input samples and outputs 128 frequency bins signals.

Further, in an embodiment, the FFT 308 may be oversampled. For example, in an embodiment, the FFT 308 may operate at an oversampling rate of $N*\frac{7}{8}$, where N is the FFT size (e.g., 128). In other words, if a 128 point FFT is used, the FFT is executed for every new 16 samples received. Thus, each time the FFT is executed, the FFT operates on 112 old samples and 16 new samples.

The pre-processor 304, windowing function 306 and FFT 308 may operate at an analysis rate. In an embodiment, the analysis rate may be a fixed rate. For example, in an embodiment, the pre-processor 304, windowing function 306 and FFT 308 may be executed by one or more digital signal processors (DSPs) that operate at a specified number of cycles per second (e.g., 5011000 cycles per second). In an example, the analysis rate may be fixed at a rate of 978.7 Hz (5011000/(320*16)=978.7 Hz), where 5011000 is the number of cycles per second, 16 is the number of samples received by the FFT 308 per FFT analysis, and 320 is the number of cycles between audio samples. Thus, in this exemplary embodiment, there are 978.7 FFT analysis performed per second. It should be noted, however, that these numbers are exemplary only and that in other implementations a different analysis rate may be used.

Referring back to FIGS. 3 and 4, the output of FFT 308 is provided to a frequency domain pre-processor 309 at block 311. The frequency domain pre-processor 309 may perform frequency domain pre-processing at the fixed analysis rate. Although the presently described embodiment is discussed with reference to a cochlear implant 100 configured for application of electrical stimulation, in other embodiments other types of devices may be used. For example, in an embodiment in which the device is a Hybrid device configured for application of electrical and acoustic stimulation, the pre-processing performed at blocks 304 and 309 may be shared for both stimulation paths (e.g., electric and acoustic paths).

The frequency bin signals may then be provide to a rate matching by interpolation (RMI) function 310 at block 412. The purpose of the RMI function 310 is to resample the FFT output (i.e., the frequency bin outputs) from the fixed analysis rate to the stimulation rate. The stimulation rate is the rate at which stimulation is applied to the recipient.

Because recipients are heterogeneous, each recipient of a cochlear implant may be provided with a different set of parameters to maximize speech reception and recipient satisfaction. This set of parameters may include the stimulation rate to be used by the cochlear implant. A clinical professional, usually an audiologist, typically selects a set of parameters, commonly referred to as a parameter map or, more simply, a MAP, that will provide the best possible sound reception for an individual recipient during a process commonly referred to as fitting the cochlear implant. Once determined, the MAP is typically stored in the sound processor of the cochlear implant and used for processing received audio signals and applying the corresponding stimulation to the recipient.

Figure 6:
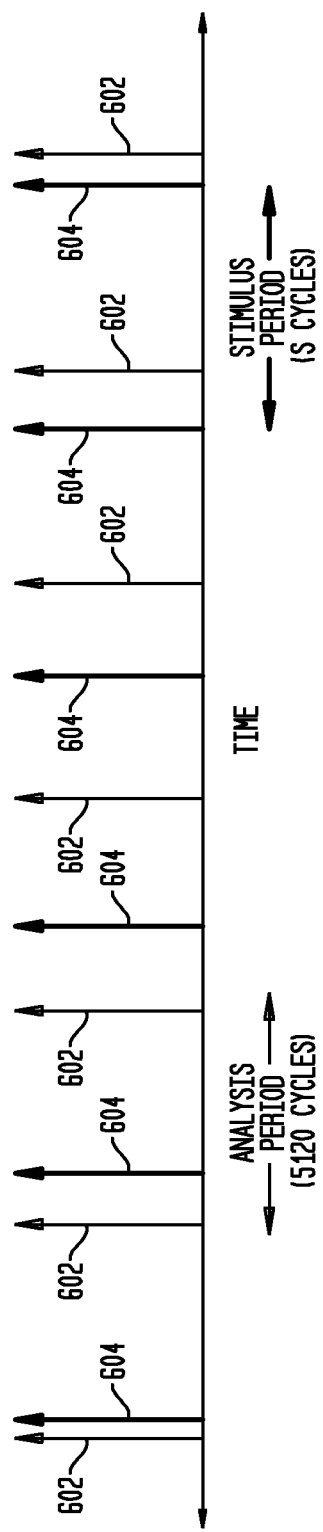
FIG. 6 provides a simplified diagram illustrating different analysis and stimulation rates, in accordance with an embodiment of the present invention.

Because the stimulation rate may vary from recipient to recipient and/or may be adjusted after the initial fitting process, the stimulation rate may be different than the analysis rate. FIG. 6 provides a simplified diagram illustrating different analysis and stimulation rates. In the illustrated example, the analysis rate is greater than the stimulation rate. The number of cycles between applications of stimulation 602 (referred to herein as the stimulation period) is greater than the number of cycles between analysis outputs 604 (referred to herein as the analysis period). Thus, in the illustrated example, the rate at which analysis outputs are provided is greater than the rate at which stimulation is applied. In other words, in the illustrated example, the FFT 308 has an output rate that is greater than the stimulation rate. The RMI function 310, which will be described in more detail below, matches the fixed analysis rate to the MAP-dependent stimulation rate.

Referring back to FIGS. 3 and 4, the RMI function block 310 provides the rate matched frequency bin outputs to a Cochlear Implant (CI) processing function 312. After application of RMI function 310 at block 412, sound processor 126 may further obtain the next 16 samples from the pre-processor 304 at block 414 and provide these new samples to windowing function 306 (block 408). As noted above, in the presently discussed embodiment, the FFT is oversampled at a rate of N*⅞, where N=128; thus, each execution of the FFT includes 112 old samples, and the 16 new samples.

The CI processing function 312 may combine the rate-matched FFT bins to create a specified number of band-pass filtered signals at block 418. For example, CI processing function 312 may combine the frequency bins using a process referred to as vector combination to create a specified number of band-pass filtered signals. In an embodiment, the cochlear implant 100 may be configured with C separate stimulation channels. For example, for an implant system providing 22 stimulation channels, CI processing function 312, at block 418, may combine the FFT frequency bins to output 22 separate band-pass filtered signals, one for each stimulation channel.

CI processing function 312 may, at block 419, perform CI specific post-processing functions, such as, for example, applying adaptive dynamic range optimization (ADRO), mapping, or other-CI specific functions for the particular implementation of the cochlear implant.

CI processing function 312 may, at block 420, further select the stimulation channels on which stimulation will be applied as well as amplitude and other specifics of the stimulation signals for application of the stimulation. CI processing function 312 may use the above-discussed MAP in determining the stimulation channels for application of the stimulation on the selected stimulation channels. CI processing function 312 may use various mechanisms for selecting the stimulation channels and specifying the stimulation signals. For example, in an embodiment, the CI processing function 312 may select a specified number of maxima (e.g., specified in the MAP) for application of stimulation. For example, cochlear implant 100 may implement ACE maxima selection or Psychoacoustic Advanced Combination Encoder (PACE) maxima selection in selecting the stimulation channels.

After determining the stimulation signals, CI processing function may encode the signals, at block 422, for transmission to the internal component 144 and provide the encoded signals to the external transmitter unit 128 for transmission. A stimulator unit 120 (FIG. 1) of internal component 144 may receive the encoded stimulation signals, decode the stimulation signals, and apply the stimulation signals via stimulating lead assembly 118, at block 424.

As noted above, in an embodiment, the RMI function 310 (block 412) matches the fixed analysis rate to the MAP-dependent stimulation rate. The RMI function 310 may perform this rate matching by interpolating each frequency bin output of the FFT 308 to a plurality of possible output times (e.g., 16 possible output times) distributed across the analysis period. The interpolated value for the output times closest matching the stimulation time is then used for determining the stimulation to be applied at the stimulation time. For example, in an embodiment, the RMI function 310 keeps track of the stimulation times relative to the analysis times to help RMI function 310 select the output time most closely matching the stimulation time.

In an embodiment, the RMI function 310 interpolates the output of each frequency bin to 16 possible output timings evenly distributed across one analysis period. The RMI function 310 may perform the resampling using a polyphase multirate Finite Impulse Response (FIR) filter that may depend, for example, on the most 3 recent FFT outputs. As such, the present embodiment will be discussed with reference to a 16× interpolation filter, in which there are 3 taps per output (i.e., where the 3 most recent outputs from the FFT are use), thus resulting in a 48 tap interpolation filter (48=16*3).

Although the present embodiment will be discussed with reference to an RMI function with 16 possible output times, in other embodiments, the RMI function may have a greater or fewer number of possible output times. Further, in other embodiments, the FIR filter may process a different number of most recent FFT outputs (e.g., the 5 most recent FFT outputs). It should also be noted that although in the presently described embodiment the interpolation filter is described as outputting a plurality of interpolated values distributed across the analysis period, in other embodiments the interpolation filter may output interpolated values distributed across a different period.

In an embodiment, the analysis timing and stimulus timing may be derived from the same clock (e.g., a 5 MHz clock). As noted above, in an embodiment, the analysis timing may be a fixed rate (e.g., 5120 cycles per analysis) and the stimulus timing may be variable.

It should be noted that although as described above, the RMI function 310 interpolates the output of each frequency bin to a plurality of output timings, in other embodiments, the RMI function 310 may initially determine which of the plurality of output times will be used for determining the value of the frequency bins at the stimulation time (i.e., the time at which stimulation is to be applied). Then, the RMI function 310 may simply compute the interpolated value for this selected output time, rather than computing the values for all output times (e.g., all 16 output timings). An exemplary embodiment in which RMI function only computes the interpolated value for the frequency bins at the selected output time will be discussed in further detail below with reference to FIG. 12.

In an embodiment, the interpolation filter harnesses some of the properties of the FFT bin outputs. Particularly, in the case of an N−1 overlap FFT (i.e., where the FFT is computed for each new received sample) the DC bin may be viewed as a low pass filter and the remaining bins of the FFT may be viewed as a frequency shifted version of this low pass filter. In the case of an FFT with a smaller overlap (e.g., N*⅞), the frequency response of the DC bin may be very similar at lower frequencies to the DC bin for the N−1 overlap FFT, but have number of images of this response at lower frequencies repeated at higher frequencies. As will be discussed in further detail below, an interpolation filter for the DC bin may be determined and that counteracts these images, so that when the interpolation filter is applied to the DC bin, the resulting combined response is similar to that of the DC bin for an N−1 overlap FFT. Once determined, this interpolation filter is replicated across all FFT bins.

As noted, the output from the DC bin of an FFT may be viewed as equal to the output of a finite impulse response (FIR) filter, where the response defines the filter taps for the FIR filter. FIGS. 6-9 will be used to explain a mechanism for determining an interpolation filter for the DC bin, in accordance with an embodiment.

Figure 7:
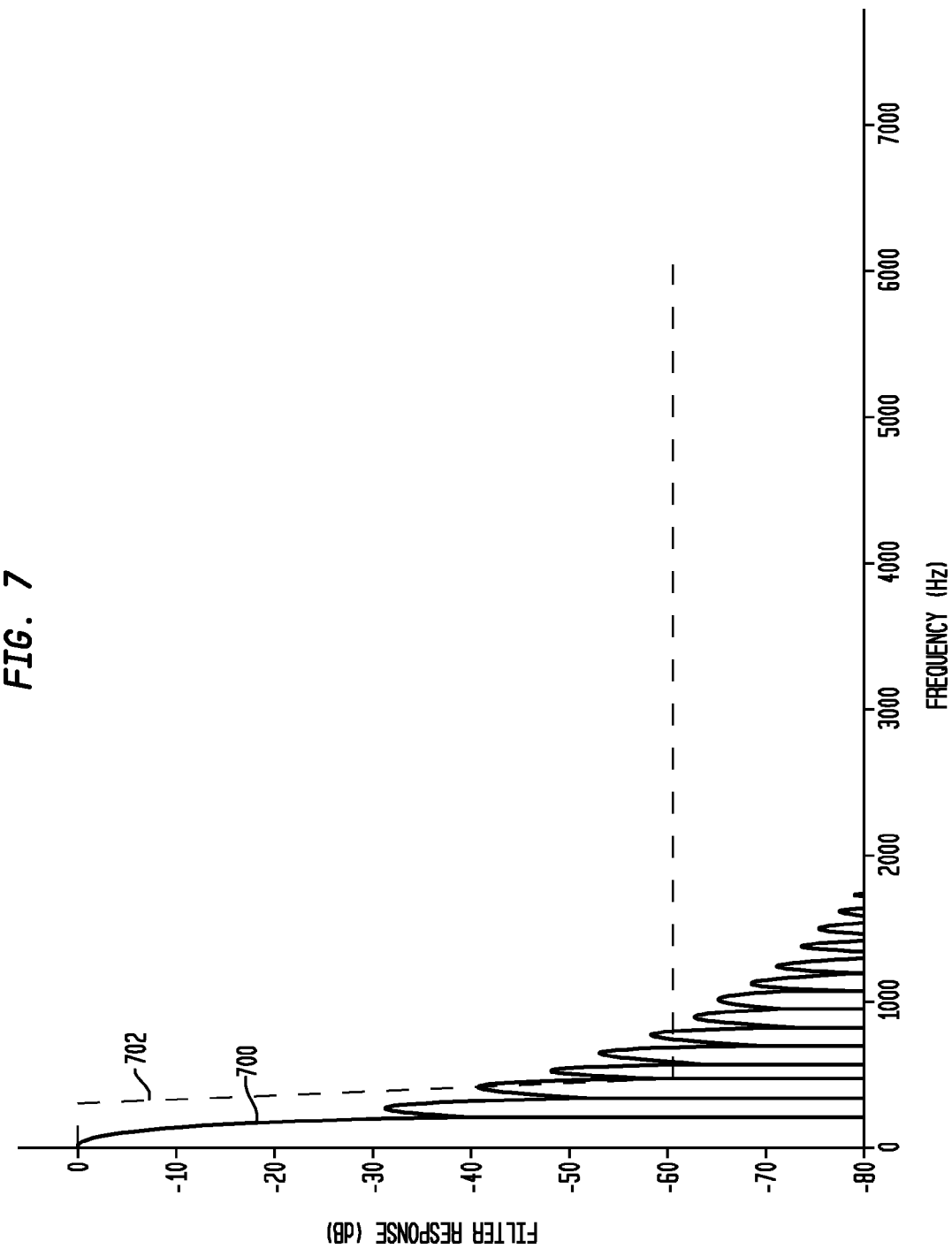
FIG. 7 illustrates an exemplary frequency response for the DC bin if the FFT is calculated with an (N−1) overlap, in accordance with an embodiment of the present invention.

FIG. 7 illustrates an exemplary frequency response 700 for the DC bin if the FFT is calculated with an (N−1) overlap, i.e., an FFT output is generated for each new received input sample (also referred to herein as the full rate DC bin). Frequency response 702 is a plot for a traditional interpolation filter. As can be seen in FIG. 7, the frequency response 702 for a traditional interpolation filter is similar to the frequency response 700 for the DC with an (N−1) overlap.

Figure 8:
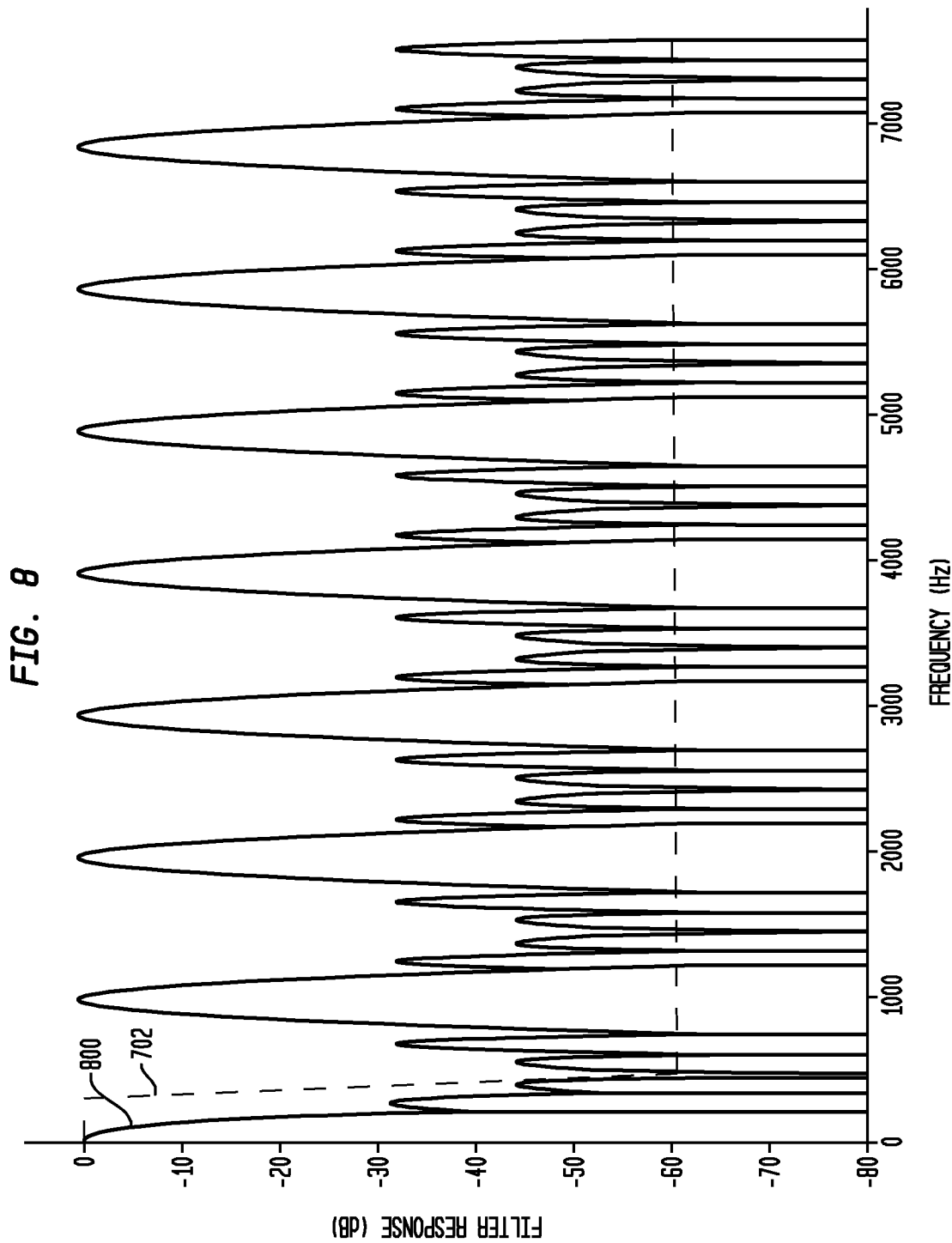
FIG. 8 illustrates an exemplary frequency response for the DC bin where the FFT is calculated for every 16 samples and N=128 (e.g., N*⅞ overlap), in accordance with an embodiment of the present invention.

As noted above, in the presently discussed embodiment, the FFT is oversampled with an overlap rate of N*⅞. FIG. 8 illustrates an exemplary frequency response 800 for the DC bin for the presently embodiment in which the FFT is calculated for every 16 samples (e.g., N*⅞ overlap). As illustrated, the frequency response 800 of the FIR filter contains images in this embodiment. For example, as illustrated, frequency response 800 has a maximum at frequency 0 Hz followed by two smaller lobes at approximately 1000 Hz. Then, images of this main lobe and the two smaller lobes are repeated at higher frequencies (e.g., an image is repeated immediately above the two smaller lobes, followed by yet another image immediately above the first image, etc.)

Figure 9A:
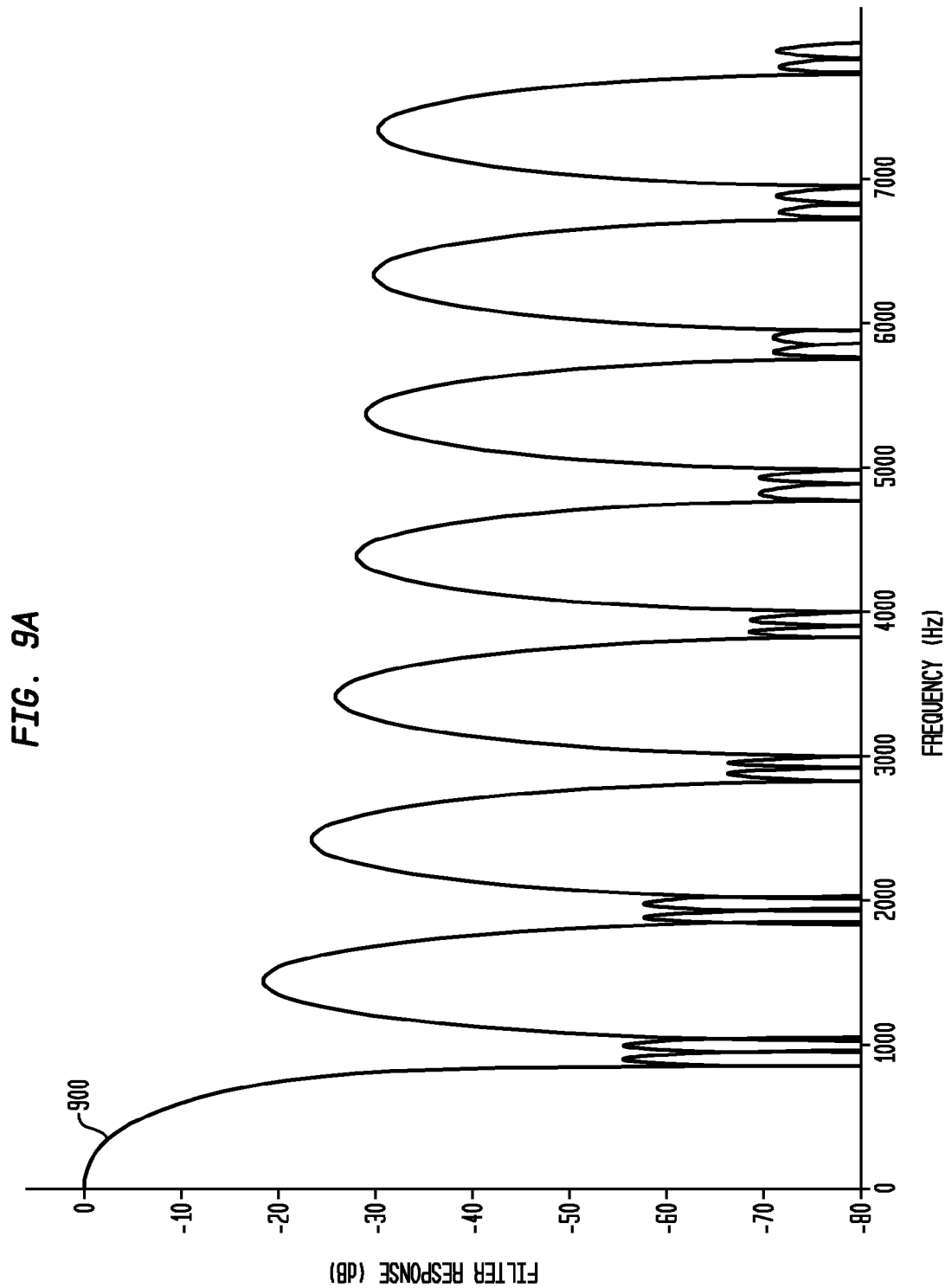
FIG. 9A illustrates an exemplary frequency response for an interpolation filter that attenuates the images of the frequency response of FIG. 8, in accordance with an embodiment of the present invention.

In an embodiment, the frequency response for the interpolation filter for the DC bin is designed to attenuate these images. FIG. 9A illustrates an exemplary frequency response 900 for such an interpolation filter that attenuates the images of the frequency response 800, in accordance with an embodiment. FIG. 9B illustrates frequency response 800 overlaid with frequency response 900. As illustrated, at the frequencies at which the images occur in frequency response 800, the interpolation filter response 900 has peaks that correspond to the minimums of frequency response 800, and has minimums that correspond to the maximums of frequency response 800. Thus, filter response 900 will have the effect of attenuating the images of frequency response 800.

Figure 10:
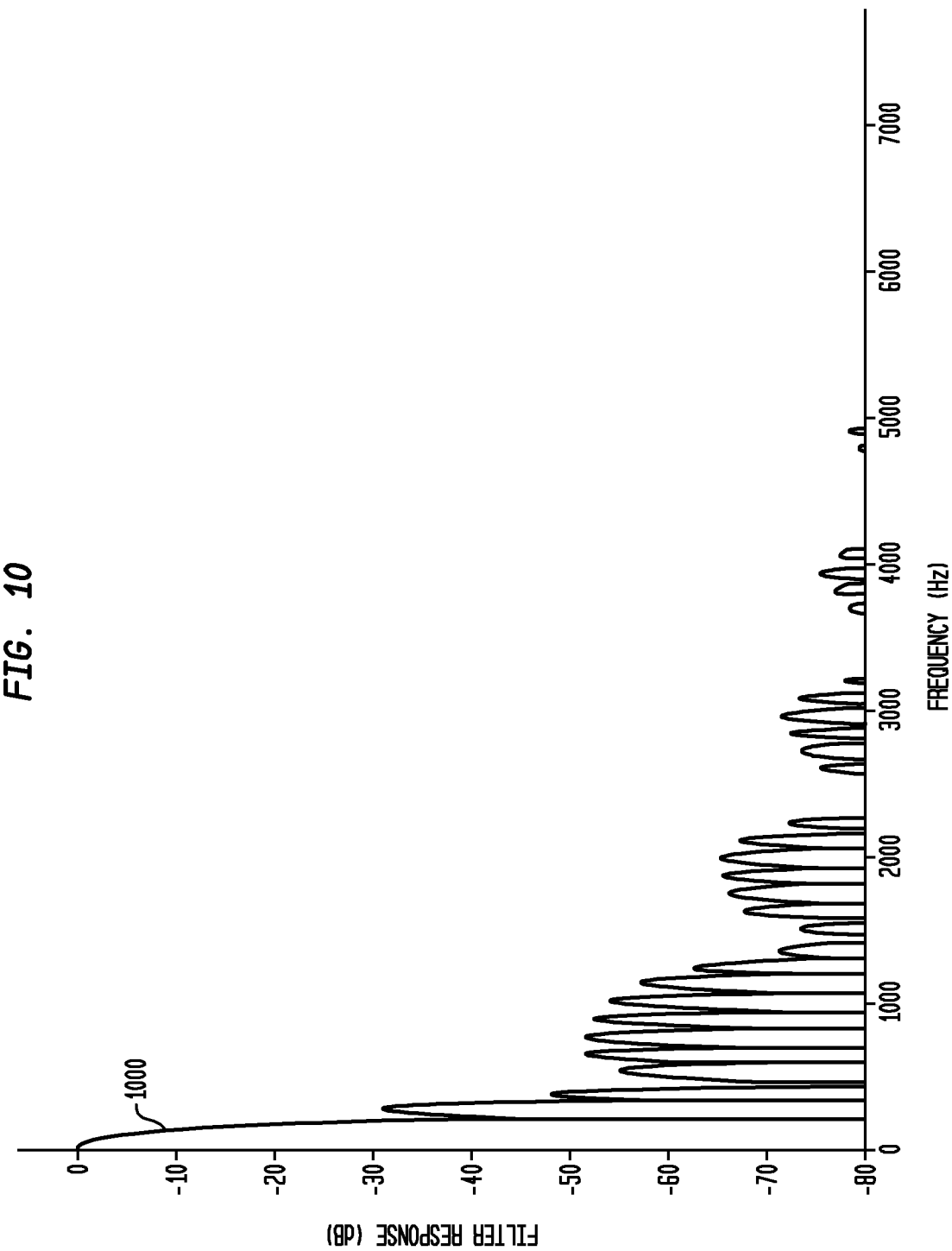
FIG. 10 illustrates the resulting frequency response when the interpolation filter of FIG. 9A is applied to the frequency response of FIG. 8, in accordance with an embodiment of the present invention.

FIG. 10 illustrates the resulting frequency response 1000 when the interpolation filter of FIG. 9A is applied to the frequency response 800. As shown, the resulting frequency response 1000 more closely matches the frequency response 700 for the DC bin with an overlap of N−1 (i.e., the FFT is calculated for each new received sample).

In an embodiment, the interpolation filter providing frequency response 900 may be designed by, for example, training a recursive least squares (RLS) filter using a white noise input, with the goal of minimizing the mean squared error between the output of the filter 1000 and the frequency response 700 for the full rate DC bin with the constraint that the resulting filter only have a specified number of taps (e.g., 48). For example, in the embodiment of FIG. 9, the interpolation filter for the DC bin is designed with the constraint that the interpolation filter have 48 taps. This equates to the illustrated frequency response 900 having 24 pins (i.e., points where the frequency response 900 is equal to 0). The number 24 pins is derived from the fact that FIG. 9 illustrates the half of the frequency response for frequencies>=0.

It should be noted, however, that this is but one example of a mechanism for designing the interpolation filter for the DC bin, and in other embodiments, other mechanisms may be used. For example, in other embodiments, the interpolation filter for the DC bin may be designed using a matrix inversion approach that solves the following formula:

$$b \approx YM^{-1},$$

where Y is the set of filter taps obtained through calculating a linear combination of time shifted windows. M contains each of these windows as its rows (the time shift is equal to the analysis rate time shift), while b is a row vector containing the r weights required to minimize the mean square error between bM and Y. For each desired output we wish Y to be equal to a time shifted window (shift=0, 1, 2 ... N/4−1). The set of taps (e.g., 3 taps) are then determined using the above formula. In yet another embodiment, the interpolation filter for the DC bin may be determined using the Parks-McClellan method of filter design or, for example, by Wiener filtering.

Figure 11:
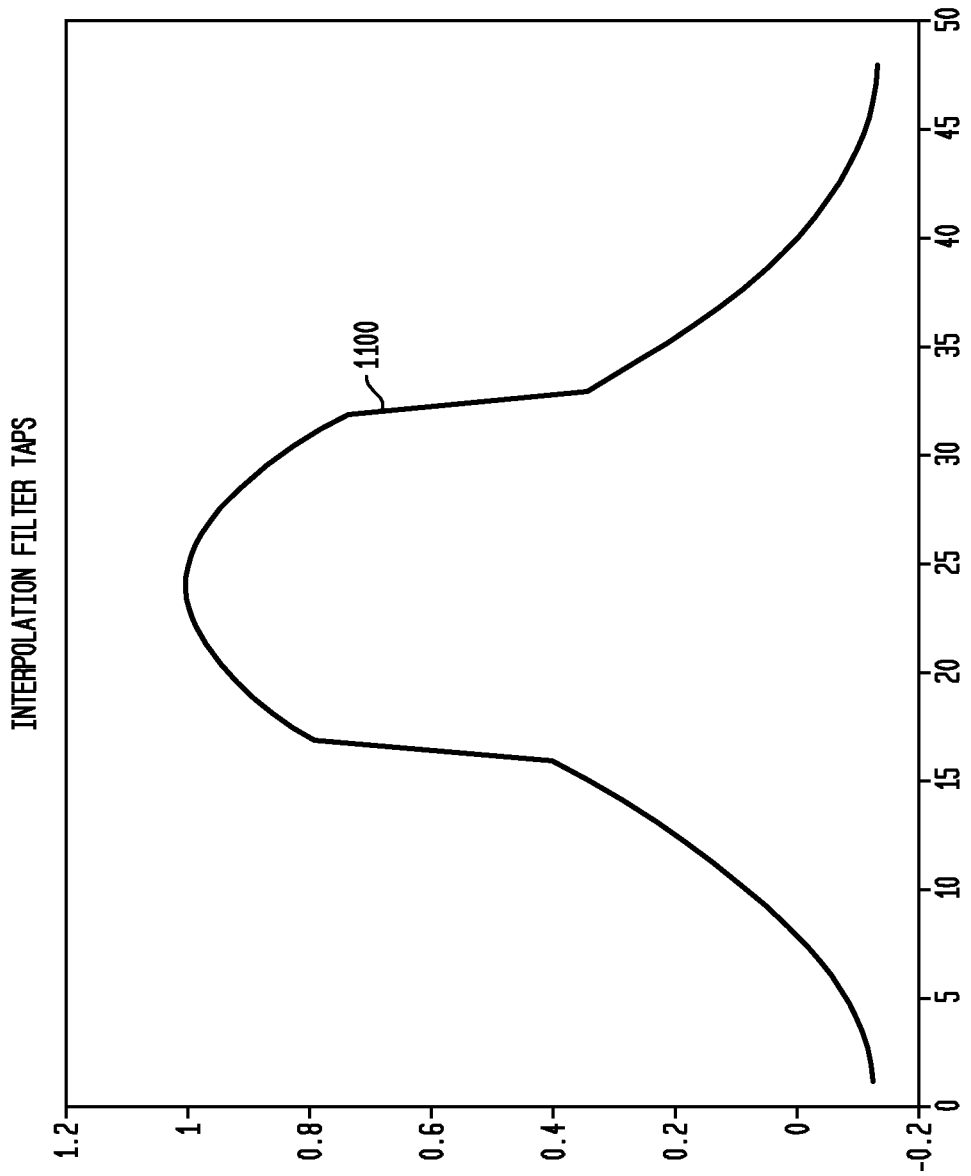
FIG. 11 illustrates the taps for an exemplary interpolation filter for the DC bin, in accordance with an embodiment of the invention.

FIG. 11 illustrates the 48 taps for an interpolation filter designed in accordance with the above procedures. This exemplary interpolation filter provides a frequency response matching frequency response 900 of FIG. 9. As illustrated, the exemplary interpolation filter has a bell shaped curve 1100 with a maximum of one (1) at tap 24. As noted above, this interpolation filter may be applied to each frequency bin output of the FFT 308. The following provides an exemplary method for application of the interpolation filter to the frequency bins of FFT 308.

As noted above, the interpolation filter of FIG. 11 was designed for the DC bin. To apply this filter to a frequency bin centered on another frequency, in an embodiment, the frequency bin is demodulated to DC. Then, the interpolation filter is applied and the output modulated back to frequency bin's center frequency.

FIG. 12 provides an exemplary flow chart for application of the RMI function at block 412 (FIG. 4). At block 1202, RMI function 310 sets a constant, k, to 0. At block 1204, RMI function 310 selects a time instant, m, of the possible M (e.g., M=16) output times which is closest to the stimulation time for application of stimulation. As noted above, in the exemplary embodiment, the interpolation filter may provide M=16 interpolated frequency bin values distributed across the analysis period. However, in other embodiments, a different value of M may be used as well as different time periods over which the interpolated values are distributed.

At block 1206, RMI function 310 demodulates frequency bin k to DC. In an embodiment, each frequency bin is demodulated to DC using the following formula:

$$\hat{x}_k = x_k \cdot e^{\frac{-j2\pi n}{N} \cdot k},$$

where k=bit number [1, 63], n=input time instant (in samples–multiple of 16), N=FFT length (128), $x_k$=output from the FFT bin k, $\hat{x}_k$=demodulated output from the FFT bin k. It should be noted that the DC bin is already at DC, and thus is not demodulated to DC.

The demodulated channels are then filtered, at block 1208, using the same filter designed for the DC bin, such as, for example, the 48 tap interpolation filter discussed above with reference to FIG. 11. In this exemplary embodiment, rather then determining the interpolated values for each of the M output times, the interpolation filter only outputs the interpolated frequency bin value for the output time, m, corresponding to the time at which stimulation is to be applied by cochlear implant 100.

After which, the filtered frequency bin output is modulated back to the center frequency for the corresponding frequency bin at block 1210. The formula for the output of each filtered FFT bin, k, at time instant m, for the present embodiment, is as follows:

$$y_k(m) = \hat{x}_k \cdot t_m \cdot e^{\frac{j2\pi m}{N} k},$$

where m=output time instant (in samples), $t_m$=vector of the 3 interpolation taps corresponding to output time instant m, and $\hat{x}_k$=vector of the last 3 demodulated outputs from the FFT bin k.

Next, if k<N/2−1, where N is the number of frequency bins (e.g., 128), at decision 1212, k is increased by 1, a block 1214, and the process returns to block 1206. Once, the interpolation filter is applied to all frequency bins (i.e., k>=N/2−1), the RMI function 310 is completed and may return to block 302 for purposes of interpolating the next FFT outputs and applying stimulation using the interpolated values. That is, referring back to FIG. 4, the process may move to blocks 414 and 418.

It should be noted that the embodiment of FIG. 12 is one exemplary method for applying the interpolation to each frequency bin of the FFT, and in other embodiments other methods may be used. For example, one or more of the illustrated steps may be combined, or the steps may be performed in a different order. Or, for example, alternative steps may be used. For example, in an embodiment, rather than demodulating the FFT bin output to DC, the speech processor may instead modulate the interpolation filter so that it is centered in the FFT bin. Further, in other embodiments, not all frequency bins (e.g., the DC bin) will be used by the cochlear implant in applying stimulation. Is such embodiments, the interpolation filter may not be applied to frequency bins (e.g., the DC bin) that are not used.

In various implementations of the subject matter described, such as the embodiment of FIG. 3, components may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device These computer programs (also known as programs, software, software applications, applications, components, or code) include machine instructions for a programmable processor, and may be implemented in a high-level procedural and/or object-oriented programming language, and/or in assembly/machine language. As used herein, the term "machine-readable medium" refers to any computer program product, computer-readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. Similarly, systems are also described herein that may include a processor and a memory coupled to the processor. The memory may include one or more programs that cause the processor to perform one or more of the operations described herein.

Embodiments of the present invention have been described with reference to several aspects of the present invention. It would be appreciated that embodiments described in the context of one aspect may be used in other aspects without departing from the scope of the present invention.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

What is claimed is:

1. A method for delivering a stimulating signal by a stimulating medical device having a plurality of electrodes, comprising:
receiving a sound signal;
applying a windowing function to the received signal;

applying a fast Fourier transform (FFT) to the received signal to obtain a first set of one or more frequency bin outputs at an analysis time;

applying an interpolation filter to a first one of the one or more frequency bin outputs to interpolate a value of the first frequency bin for a stimulation time;

applying the interpolation filter to a second one of the one or more frequency bin outputs to interpolate a value of the second frequency bin for the stimulation time; and delivering a stimulation signal at the stimulation time by the stimulation medical device via at least one of the electrodes using one or more of the interpolated values of the first and second frequency bins.

2. The method of claim 1, further comprising:

converting the received sound signal from analog to digital to provide a sequence of digital samples of the received sound signal; and wherein the FFT is applied with a specified overlap rate, and where applying the FFT comprises:

providing a specified number of the digital samples to the FFT in accordance with the specified overlap rate;

applying the FFT to the provided digital samples such that the FFT is applied to the specified number of digital samples and a plurality of digital samples previously used in applying the FFT.

3. The method of claim 2, wherein applying the interpolation filter to a first frequency bin output comprises:

applying the interpolation filter to a current first frequency bin output and a plurality of prior first frequency bin outputs.

4. The method of claim 1, wherein the interpolation filter is designed to reduce the amplitude of one or more images appearing in a frequency response corresponding to the first frequency bin.

5. The method of claim 4, wherein the first frequency bin is the DC frequency bin for the FFT.

6. The method of claim 1, wherein applying the interpolation filter to the second frequency bin comprises:

demodulating the frequency bin output;

applying the interpolation filter to the demodulated frequency bin output; and modulating the filtered frequency bin output to provide the interpolated value for the second frequency bin.

7. The method of claim 1, wherein applying the interpolation filter to the second frequency bin comprises:

modulating the interpolation filter to a frequency corresponding to the second frequency bin; and applying the modulated interpolation filter to the second frequency bin output.

8. The method of claim 1, wherein the windowing function comprises a Hanning window.

9. The method of claim 1, wherein the stimulating medical device is a cochlear implant.

10. A stimulating medical device for delivering stimulation signals to a recipient, comprising:

at least one electrode configured to deliver stimulation signals to the recipient;

a sound input device configured to receive a sound signal;

a sound processor comprising:

a windowing functional block configured to apply a window to the received signal to generate a windowed received signal;

an fast Fourier transform (FFT) functional block configured to apply an FFT to the windowed received signal to obtain a first set of one or more frequency bin outputs at an analysis time;

a interpolation functional block configured to apply an interpolation filter to a first one of the one or more frequency bin outputs to interpolate a value of the first frequency bin for a stimulation time; and apply the interpolation filter to a second one of the one or more frequency bin outputs to interpolate a value of the second frequency bin for the stimulation time; and a stimulator unit configured to deliver a stimulation signal at the stimulation time by the stimulation medical device via at least one of the electrodes using one or more of the interpolated values of the first and second frequency bins.

11. The stimulating medical device of claim 10, further comprising:

an analog to digital converter configured to convert the received sound signal from analog to digital to provide a sequence of digital samples of the received sound signal; and wherein the FFT functional block is configured to apply the FFT with a specified overlap rate such that the FFT is applied to a plurality of new digital samples received from the analog to digital converter and a plurality of digital samples previously used in applying the FFT.

12. The stimulating medical device of claim 11, wherein the interpolation functional block is configured to apply the interpolation filter to a current first frequency bin output and a plurality of prior first frequency bin outputs.

13. The stimulating medical device of claim 10, wherein the interpolation filter is designed to reduce the amplitude of one or more images appearing in a frequency response corresponding to the first frequency bin.

14. The stimulating medical device of claim 13, wherein the first frequency bin is the DC frequency bin for the FFT.

15. The stimulating medical device of claim 10, wherein the interpolation functional block is configured to apply the interpolation filter to the second frequency bin by demodulating the frequency bin output; apply the interpolation filter to the demodulated frequency bin output; and modulate the filtered frequency bin output to provide the interpolated value for the second frequency bin.

16. The stimulating medical device of claim 10, wherein the interpolation functional block is configured to apply the interpolation filter to the second frequency bin by modulating the interpolation filter to a frequency corresponding to the second frequency bin; and applying the modulated interpolation filter to the second frequency bin output.

17. The stimulating medical device of claim 10, wherein the windowing function comprises a Hanning window.

18. The stimulating medical device of claim 10, wherein the stimulating medical device is a cochlear implant.

19. A method for delivering a stimulating signal by a stimulating medical device having a plurality of electrodes, comprising:

receiving a sound signal;

converting the received sound signal from analog to digital to provide a sequence of digital samples of the received sound signal;

applying a fast Fourier transform (FFT) to the received signal with a specified overlap rate to obtain a first set of one or more frequency bin outputs at an analysis time;

applying an interpolation filter to a first one of the one or more frequency bin outputs to interpolate a value of the first frequency bin for a stimulation time;

applying the interpolation filter to a second one of the one or more frequency bin outputs to interpolate a value of the second frequency bin for the stimulation time; and delivering a stimulation signal at the stimulation time by the stimulation medical device via at least one of the electrodes using one or more of the interpolated values of the first and second frequency bins.

20. The method of claim 19,
wherein applying the FFT comprises:
providing a specified number of the digital samples to the FFT in accordance with the specified overlap rate;
applying the FFT to the provided digital samples such that the FFT is applied to the specified number of digital samples and a plurality of digital samples previously used in applying the FFT.

21. The method of claim 20, wherein applying the interpolation filter to a first frequency bin output comprises:
applying the interpolation filter to a current first frequency bin output and a plurality of prior first frequency bin outputs.

22. The method of claim 19, wherein the interpolation filter is designed to reduce the amplitude of one or more images appearing in a frequency response corresponding to the first frequency bin.

23. The method of claim 22, wherein the first frequency bin is the DC frequency bin for the FFT.

24. The method of claim 19, wherein applying the interpolation filter to the second frequency bin comprises:
demodulating the frequency bin output;
applying the interpolation filter to the demodulated frequency bin output; and
modulating the filtered frequency bin output to provide the interpolated value for the second frequency bin.

25. The method of claim 19, wherein applying the interpolation filter to the second frequency bin comprises:
modulating the interpolation filter to a frequency corresponding to the second frequency bin; and
applying the modulated interpolation filter to the second frequency bin output.

26. The method of claim 19, further comprising:
applying a windowing function to the received signal prior to applying the FFT.

27. A stimulating medical device for delivering stimulation signals to a recipient, comprising:
at least one electrode configured to deliver stimulation signals to the recipient;
a sound input device configured to receive a sound signal;
a sound processor comprising:
an analog to digital converter configured to convert the received sound signal from analog to digital to provide a sequence of digital samples of the received sound signal;
a fast Fourier transform (FFT) functional block configured to apply an FFT to the received signal with a specified overlap rate to obtain a first set of one or more frequency bin outputs at an analysis time;
a interpolation functional block configured to apply an interpolation filter to a first one of the one or more frequency bin outputs to interpolate a value of the first frequency bin for a stimulation time; and apply the interpolation filter to a second one of the one or more frequency bin outputs to interpolate a value of the second frequency bin for the stimulation time; and
a stimulator unit configured to deliver a stimulation signal at the stimulation time by the stimulation medical device via at least one of the electrodes using one or more of the interpolated values of the first and second frequency bins.

28. The stimulating medical device of claim 27, wherein the FFT functional block is configured to apply the FFT with the specified overlap rate such that the FFT is applied to a plurality of new digital samples received from the analog to digital converter and a plurality of digital samples previously used in applying the FFT.

29. The stimulating medical device of claim 28, wherein the interpolation functional block is configured to apply the interpolation filter to a current first frequency bin output and a plurality of prior first frequency bin outputs.

30. The stimulating medical device of claim 27, wherein the interpolation filter is designed to reduce the amplitude of one or more images appearing in a frequency response corresponding to the first frequency bin.

31. The stimulating medical device of claim 27, wherein the interpolation functional block is configured to apply the interpolation filter to the second frequency bin by demodulating the frequency bin output; apply the interpolation filter to the demodulated frequency bin output; and modulate the filtered frequency bin output to provide the interpolated value for the second frequency bin.

32. The stimulating medical device of claim 27, wherein the interpolation functional block is configured to apply the interpolation filter to the second frequency bin by
modulating the interpolation filter to a frequency corresponding to the second frequency bin; and applying the modulated interpolation filter to the second frequency bin output.

33. The stimulating medical device of claim 27, further comprising:
a windowing functional block configured to apply a window to the received signal and provide the windowed signal to the FFT functional block.

34. The stimulating medical device of claim 27, wherein the stimulating medical device is a cochlear implant.

* * * * *